United States Patent [19]

Kiss et al.

[11] 4,043,937

[45] Aug. 23, 1977

[54] HALOGEN DERIVATIVES OF ASCORBIC ACID AND D-ARABOASCORBIC ACID ANTIOXIDANTS

[75] Inventors: Joseph Kiss, Arlesheim, Switzerland; Klaus Peter Berg, Grenzach-Wylen, Germany

[73] Assignee: Hoffmann-La Roche Inc., Nutley, N.J.

[21] Appl. No.: 681,083

[22] Filed: Apr. 28, 1976

[30] Foreign Application Priority Data

May 3, 1975 Switzerland .......................... 5741/75

[51] Int. Cl.² .......................................... C07D 307/32
[52] U.S. Cl. .................................. 252/407; 260/343.7; 260/340.9 R; 260/483; 260/535 R; 260/347.8
[58] Field of Search ............... 260/343.6, 343.7, 347.8; 252/407

[56] References Cited

U.S. PATENT DOCUMENTS

| | | | |
|---|---|---|---|
| 3,075,998 | 1/1963 | Lardelli et al. | 260/343.6 |
| 3,250,790 | 5/1966 | Kläui et al. | 260/343.7 |
| 3,637,772 | 1/1972 | Kaui et al. | 260/398.5 |
| 3,758,513 | 9/1973 | Heiba et al. | 260/343.3 |

*Primary Examiner*—Cecilia M. S. Jaisle
*Attorney, Agent, or Firm*—Samuel L. Welt; Bernard S. Leon; William H. Epstein

[57] ABSTRACT

The halogen derivatives of ascorbic acid and D-araboascorbic acid useful as antioxidants as well as a method for stabilizing oxidation-sensitive organic materials by incorporating said derivatives in oxidation sensitive materials.

9 Claims, No Drawings

HALOGEN DERIVATIVES OF ASCORBIC ACID AND D-ARABOASCORBIC ACID ANTIOXIDANTS

SUMMARY OF INVENTION

In accordance with this invention, it has been discovered that compounds of the tautomeric formulae

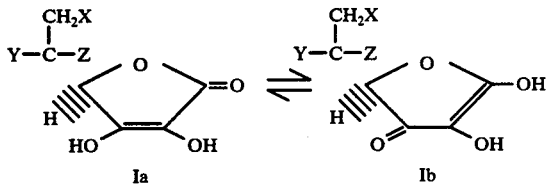

wherein X is halogen; and one of Y and Z is hydrogen and the other is hydroxy; with the provision that when Y is hydroxy and Z is hydrogen, X is either chlorine or bromine,
and salts of these compounds are useful as antioxidants for oxidation sensitive materials.

DETAILED DESCRIPTION

The halogen derivatives provided by the present invention are derivatives of L-ascorbic acid or its 5-enantiomer, D-araboascorbic acid, wherein the hydroxy group in the 6-position is replaced by a halogen atom. The following partial structures accordingly come into consideration:

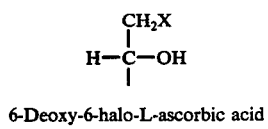

6-Deoxy-6-halo-L-ascorbic acid

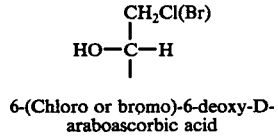

6-(Chloro or bromo)-6-deoxy-D-araboascorbic acid

The term "halogen" used herein includes fluorine, chlorine, bromine and iodine.

The term "salts" used herein will be understood to means salts of the acids of formulae Ia and Ib with bases. Examples of such salts are metal salts such as alkali metal salts (e.g. the sodium, potassium and lithium salts), alkaline earth metal salts (e.g. the calcium salts), other metal salts (e.g. the magnesium, aluminium, zinc and iron salts), the ammonium salts and organic amino salts (e.g. the triethylammonium salts).

According to one process provided by this invention, the compounds of formulae Ia and Ib in which the symbol X is chlorine or bromine atom and their salts are manufactured by reacting a compound of the tautomeric formulae:

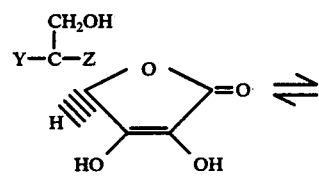

wherein Y and Z are as above; with hydrogen chloride or hydrogen bromide and, if desired, converting the product into a salt.

The reaction of L-ascorbic acid or D-araboascorbic acid of formula IIa or IIb with hydrogen chloride or hydrogen bromide in accordance with the aforementioned process is preferably carried out in solution in a lower alkanecarboxylic acid (e.g. formic acid, acetic acid, propionic acid etc). The reaction is preferably carried out in a pressure vessel with slight over-pressure (e.g. up to about 2 atmospheres). The reaction is preferably carried out within a temperature range of from room temperature up to about 100° C.

According to another process of this invention, the compounds of formula Ia and Ib in which Y is hydrogen and Z is hydroxy and their salts are manufactured by isomerising and lactonising a compound of the general formula:

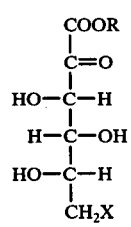

wherein X is as above; and R is hydrogen or lower alkyl, by treatment with an acidic agent and, if desired, converting the product into a salt.

Starting from compounds of formula III there is obtained a 6-deoxy-6-halo-L-ascorbic acid derivative of formula Ia or Ib. The symbol R in formula III preferably is lower alkyl group (e.g. methyl or ethyl). The compounds of formula III are advantageously prepared from a ketal of the general formula:

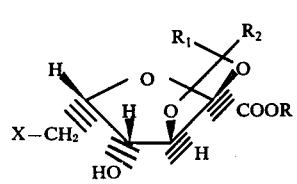

wherein X and R are as above and $R_1$ and $R_2$ taken alone are lower alkyl or taken together are together lower alkylene.
In this case, the lower alkyl groups which contain from 1 to 6 carbon atoms denoted by the symbols $R_1$ and $R_2$ are preferably methyl or ethyl. Where the symbols $R_1$ and $R_2$ together represent lower alkylene, which contains from 2 to 6 carbon atoms, ethylene is preferred.

The ketals of formula IV are treated with a hydrolytic cleavage agent. As such agents there may be mentioned, in particular, acidically reacting substances; for example, mineral acids such as hydrochloric acid and sulfuric acid, strong organic acids such as formic acid and oxalic acid and acid salts of the aforementioned acids such as potassium bisulfate. Further, one of the conventional sulfonated cation-exchange resins based on styrene/divinylbenzene or phenol/formaldehyde (e.g. Amberlite, Dowex or Wofatit) is advantageously used for the cleavage of a ketal of formula IV. The hydrolytic cleavage is preferably carried out in an aqueous medium and at a temperature of from room temperature to the reflux temperature of the mixture.

An L-gulosonic acid derivative of formula III obtained is subsequently isomerised and lactonised by treatment with an acidic agent, a desired compound of formula Ia or Ib being obtained. As the acidic agents there are preferably used the same agents as mentioned earlier for the hydrolytic cleavage of a ketal of formula IV. It is especially preferred to convert a ketal of formula IV with the aid of an acidic agent directly into a compound of formula Ia or Ib without isolation of an L-gulosonic acid derivative of formula III obtained. The conversion of an L-gulosonic acid derivative of formula III into a compound of formula Ia or Ib is preferably carried out, as in hydrolytic cleavage of a ketal of formula IV, in an aqueous medium and at a temperature between room temperature and the reflux temperature of the mixture.

The ketals of formula IV can be obtained in accordance with the following formula scheme in which the symbols R, $R_1$, $R_2$ and X are as above:

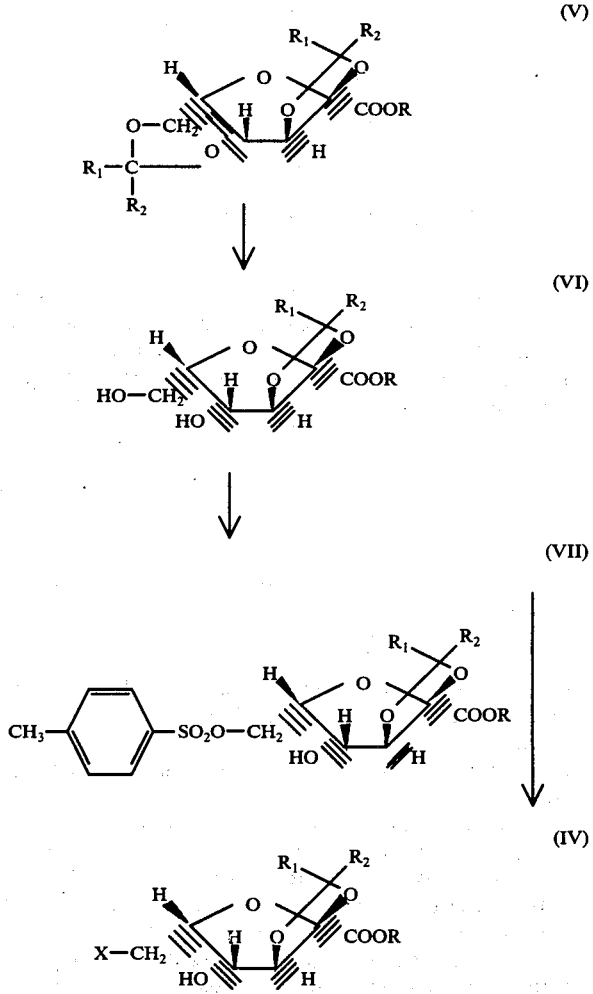

Referring to this reaction scheme, a diketal of formula V, preferably methyl 2,3:4,6-diisopropylidene-L-gulosonate, is subjected to a selective ketal cleavage in an aqueous medium, preferably by heating with copper acetate. A selective ketal cleavage can also be carried out by heating with a dilute lower alkanecarboxylic acid such as acetic acid. A monoketal of formula VI obtained can now be reacted with a tri(lower alkyl)-phosphate and triphenylphosphine in the presence of carbon tetrachloride or bromine, preferably while warming, in order to introduce a chlorine or bromine atom into the 6-position. In order to introduce a fluorine or iodine atom into the 6-position, there is first prepared a 6-tosyloxy derivative of formula VII, conveniently by treating a pyridine solution of a monoketal of formula VI with p-toluenesulphonyl chloride. Such a 6-tosyloxy derivative is then heated in an inert solvent (e.g. acetone, methyl propyl ketone or dimethylformamide) with an alkali metal halide (e.g. potassium fluoride or sodium iodide).

The ketals of formula IV can be purified by conventional procedures such as by chromatography on aluminium oxide or silica gel with a suitable solvent (e.g. ethyl acetate).

The conversion of the compounds of formulae Ia and Ib into their salts is carried out in the usual manner by neutralisation of the acids of formulae Ia and Ib preferably in aqueous solution, with an appropriate base; for example sodium hydroxide, calcium hydroxide, ammonium hydroxide or a carbonate or bicarbonate such as sodium carbonate or potassium bicarbonate.

The compounds of formula Ia and Ib and their salts are crystalline solid substances which have a relatively good solubility in water, lower alkanols (e.g. methanol and ethanol), lower ethers (e.g. diethyl ether, tetrahydrofuran and dioxane) and lower esters (e.g. ethyl acetate) and which have a relatively poor solubility in lower hydrocarbons (e.g. n-hexane, n-heptane, petroleum ether and ligroin). In lower nitroalkanes (e.g. nitromethane and nitroethane) they have a relatively poor solubility at room temperature and a relatively good solubility at higher temperatures (e.g. at 100° C).

The compounds of formula Ia and Ib and their salts are valuable antioxidants and can be used for the stabilization of oxidation-sensitive organic materials. Any conventional oxidation sensitive material can be stabilized by use of the compounds of formula Ia and Ib and their salts. Such materials include, for example, fats, oils, oxidisable hydrocarbons, including polymeric hydrocarbons, terpenes, and the like, petroleum derivatives such as waxes, vitamins and the like. 6-Chloro- and 6-bromo-6-deoxy-L-ascorbic acid are especially active.

In general, the compounds of formulae Ia and Ib and their salts are added to the materials to be stabilized in amounts of about 0.001 wt.% to about 0.1 wt.% based on the weight of the oxidation-sensitive material. However, higher and lower amounts can also be used.

The expression "fats and oils" used herein includes animal oils, vegetable oils, mineral oils, waxes, lubricating agents, fats and the like; for example, lard, cottonseed oil, ground nut oil, lanolin, mutton tallow, beef tallow, linseed oil, cod liver oil, caster oil, coconut oil, palm oil, corn oil, paraffin oil, carnauba wax, paraffin wax, beeswax, olive oil, mineral oils, ethereal oils, citrus oils, mono-, di- and triglycerides of various saturated and unsaturated fatty acids, as well as materials which have an essential content of these fats and oils such as fish meal, various kinds of animal feed, milk or milk products, egg powder, mayonnaise, butter, margarine, chocolate, salad dressings and the like.

In order to demonstrate the antioxidant activity of the halogen derivatives provided by this invention, 6-chloro-6-deoxy-L-ascorbic acid and 6-bromo-6-deoxy-L-ascorbic acid, which have a toxicity in the mouse ($LD_{50}$) of 5640 mg/kg and greater than 5000 mg/kg (24 hours after a single administration), respectively, were dissolved in various edible oils (0.05 wt.%). 10 g from each sample, as well as from controls, were placed in Petri dishes in a rotary air-drying oven for the time given hereinafter or at the temperatures given hereinafter and the peroxide number was subsequently measured. The results are compiled in the following Table:

Table

| | Peroxide number | | | | | | | | |
|---|---|---|---|---|---|---|---|---|---|
| | Arachis oil, 80° C | | | Sunflower oil, 65° C | | | Soya oil, 65° C | | |
| Antioxidant | 2 Days | 3 Days | 4 Days | 2 Days | 3 Days | 4 Days | 2 Days | 3 Days | 4 Days |
| 6-Chloro-6-deoxy-L-ascorbic acid | | 28.4 | | | 13.5 | | | 2.4 | |
| Control | | 66.5 | | | 47.0 | | | 22.7 | |
| 6-Bromo-6-deoxy-L-ascorbic acid | 4.6 | 18.3 | 40.7 | 6.0 | 13.5 | 33.5 | 1.0 | 1.9 | 2.5 |
| Control | 34.4 | 66.0 | 400 | 27.8 | 50.0 | 72.1 | 9.5 | 29.0 | 56.6 |

Surprisingly, the halogen derivatives provided by this invention have superior stabilizing properties than that of L-ascorbic acid (e.g. in aqueous solution). This fact can be demonstrated by means of the following experiment:

1 and 5% aqueous solutions of 6-chloro-6-deoxy-L-ascorbic acid and of L-ascorbic acid were stored at room temperature for 48 hours and subsequently subjected to thin-layer chromatographical analysis. Whilst in the case of the L-ascorbic acid solutions decomposition products (e.g. furan-α-carboxylic acid) were clearly detectable as corresponding spots in the thin-layer chromatogram, no decomposition products appeared in the case of the 6-chloro-6-deoxy-L-ascorbic acid solutions.

It will be appreciated from the foregoing that the invention also includes within its scope (a) a method for the stabilization of oxidation-sensitive organic materials which method comprises treating said materials with a compound of the tautomeric formulae I$a$ and I$b$ hereinbefore or with a salt thereof, and (b) a mixture of an oxidation-sensitive organic material with a compound of the tautomeric formulae I$a$ and I$b$ hereinbefore or with a salt thereof.

The following Examples illustrate the process provided by the present invention: In the Examples, Amberlite IRC 120 is a cationic ion exchange resin on a polystyrene basis containing —$SO_2OH$ groups. The petroleum ether utilized in these Examples had a boiling point of about 35° to 55° C.

EXAMPLE 1

360 g of L-ascorbic acid in 1000 ml of formic acid are treated in a pressure vessel at 50° C with 145 g of hydrogen chloride gas in such a manner that the dosage velocity amounts to about 6.6 g per hour and the pressure amounts to about 0.4 to 0.6 atmospheres. Subsequently, the black mass obtained is evaporated at 60° C to a thick, pitch-like paste. This paste is stirred with about 2 liters of water at 60° C for 30 minutes. Subsequently, the water is evaporated off at 60° C under reduced pressure. The solid residue obtained is again dissolved in 2 liters of water, stirred at 60° C for 30 minutes and evaporated to dryness under reduced pressure at this temperature. This procedure is repeated once again. The residue is dissolved in 1.4 liters of water and extracted at room temperature 6 times with 1 liter of ethyl acetate each time. The combined ethyl acetate extracts are stirred with 20 g of active carbon for 15 minutes and subsequently filtered. The filtrate is freed from entrained water, dried over about 200 g of sodium sulfate, filtered and evaporated under reduced pressure at 40° C. The residue is dissolved in 600 ml of nitromethane at 80° C and filtered. The filter residue is back-washed with 100 ml of hot nitromethane (80° C). The combined nitromethane solutions are cooled to room temperature and the crystals obtained are filtered off. The crystals are dissolved at 80° C in 600 ml of nitromethane, treated with 5 g of active carbon and, after stirring for about 15 minutes at 80° C, filtered. The filter residue is washed with 100 ml of hot nitromethane (80° C). The combined nitromethane solutions are left to stand overnight at room temperature. The crystals obtained are filtered off and dissolved in 600 ml of nitromethane at about 70° C, treated with 5 g of active carbon and, after stirring for 15 minutes, filtered. The filter residue is washed with 100 ml of hot nitromethane (60° C). The combined nitromethane solutions are left to stand overnight at room temperature. The white crystals obtained are filtered off, dispersed in 100 mls of nitromethane and subsequently filtered. The thus-purified crystals are dried at 60° C under reduced pressure and further dried at 60° C for 48 hours under strongly reduced pressure (about 0.3 mmHg). There is obtained 6-chloro-6-deoxy-L-ascorbic acid of melting point 144° C.

| Analysis: | C | H | Cl |
|---|---|---|---|
| Calculated for $C_6H_7O_5Cl$: | 37.04 | 3.68 | 18.22 |
| Found: | 37.12 | 3.68 | 17.83 |

$[\alpha]_D^{25} = +25.4°$ (ethyl acetate; about 6 g/l); +6.4° (water; about 6 g/l).

EXAMPLE 2

By replacing the hydrogen chloride used in Example 1 with 80 g of hydrogen bromide, there is obtained under essentially the same conditions as Example 1 6-bromo-6-deoxy-L-ascorbic acid of melting point 175° – 176° C; $[\alpha]_D^{25} = -7.3°$ (water; c = 1).

| Analysis: | C | H | Br |
|---|---|---|---|
| Calculated for $C_6H_7O_5Br$: | 30.15 | 2.95 | 33.43 |
| Found: | 30.14 | 2.83 | 33.49 |

EXAMPLE 3

45 g of methyl 6-chloro-2,3-isopropylidene-L-gulosonate in 2250 ml of water are treated while stirring with 20 g of Amberlite IRC 120 (H+ form) in a three-necked flask provided with a stirrer and reflux condenser. The mixture is subsequently heated under reflux for 5 hours. The mixture is cooled and filtered. The filtrate is concentrated under reduced pressure to about 500 ml and extracted ten times with 100 ml of ethyl acetate each time. The combined ethyl acetate extracts are dried over sodium sulphate, filtered and concentrated under reduced pressure at 40° C. The residue is dissolved in 150 ml of hot nitromethane, treated with 1 g of active carbon and filtered while hot. After standing for 2 hours in a refrigerator, the crystals formed are filtered off, washed with nitromethane and dried under strongly reduced pressure at 60° C for 48 hours. There is obtained 6-chloro-6-deoxy-L-ascorbic acid as colorless crystals which melt at 144° – 145° C; $[\alpha]_D^{25°} = +3.92°$ (water; c = 0.816%).

EXAMPLE 4

20 g of methyl 2,3:4,6-diisopropylidene-L-gulosonate are suspended in 600 ml of distilled water in a round-bottomed flask provided with a reflux condenser and treated with 80 mg of copper acetate. The mixture is heated under reflux for about 15 minutes and subsequently evaporated to dryness under reduced pressure at about 60° C. The residue is suspended in 200 ml of ethyl acetate, treated with 1 g of active carbon and filtered. The filtrate is purified by column chromatography on silica gel with ethyl acetate. There is obtained methyl 2,3-isopropylidene-L-gulosonate as a colorless oil.

EXAMPLE 5

A solution of 65.1 g of triphenylphosphine in 660 ml of carbon tetrachloride is added in one portion while stirring to a solution of 20.6 g of methyl 2,3-isopropylidene-L-gulosonate in 330 ml of triethylphosphate in a four-necked flask provided with a thermometer, reflux condenser, calcium chloride tube and stirrer. The mixture is heated under reflux for 5 minutes and subsequently cooled to room temperature. The mixture is filtered and the filtrate concentrated under strongly reduced pressure. The residue is treated with 1000 ml of diethyl ether and the triphenylphosphine oxide which crystallises out is filtered off. The filtrate is evaporated under reduced pressure. The residue is treated once again with 150 ml of diethyl ether and freed from crystallised-out triphenylphosphine oxide by filtration. The filtrate is concentrated. The residue is dissolved in 100 ml of ethyl acetate and purified by column chromatography on silica gel with ethyl acetate. There is obtained methyl 6-chloro-2,3-isopropylidene-L-gulosonate of melting point 105° – 107° C.

EXAMPLE 6

A solution of 15 g of methyl 6-fluoro-2,3-isopropylidene-L-gulosonate in 750 ml of water is treated while stirring with 10 g of Amberlite IRC 120 (H+ form) in a three-necked flask provided with a stirrer and reflux condenser. The mixture is heated under reflux conditions for 4.5 hours, subsequently cooled, filtered and concentrated to about 200 ml under reduced pressure at 50° C. The residue is extracted six times with 100 ml of ethyl acetate each time. The combined ethyl acetate extracts are dried over sodium sulfate, filtered and evaporated under reduced pressure at 40° C. The residue is dissolved in 45 ml of hot nitromethane, treated with 0.5 g of active carbon and filtered. The filtrate is concentrated to 20 ml and left to stand firstly at room temperature and subsequently for 2 hours in a refrigerator. The crystals formed are filtered off and washed with a small amount of nitromethane and petroleum ether. The residue is dissolved in 25 ml of warm nitromethane, treated with 0.5 g of active carbon and filtered. The filtrate is left to stand for 2 hours in a refrigerator, the crystals formed are filtered off, washed with a small amount of nitromethane and petroleum ether and dried at 60° C for 48 hours under strongly reduced pressure. There is obtained 6-deoxy-6-fluoro-L-ascorbic acid as colorless crystals of melting point 140° – 142° C.

EXAMPLE 7

A solution of 15.9 g of methyl 2,3-isopropylidene-L-gulosonate in 210 ml of absolute pyridine is treated portionwise at a temperature of 2°-5° C within 1 hour with 12.8 g of p-toluenesulphonyl chloride in a four-necked flask provided with a thermometer, calcium chloride tube and stirrer. The mixture is subsequently stirred at room temperature for 16 hours and then evaporated under reduced pressure at 50° C. The residue is treated with 1 liter of distilled water and shaken for 1 hour. The mixture is filtered. The filter cake is washed well with distilled water and dried under reduced pressure at 70° C. The dried filter cake is dissolved in 200 ml of hot ethanol, treated with 1 g of active carbon and filtered. The filtrate is left to stand firstly at room temperature and subsequently for 2 hours in a refrigerator. The separated crystals are filtered off, washed with a small amount of ice-cold ethanol and dried under reduced pressure at 70° C. There is obtained methyl 2,3-isopropylidene-6-tosyl-L-gulosonate of melting point 127° – 128° C.

EXAMPLE 8

A solution of 40 g of methyl 2,3-isopropylidene-6-tosyl-L-gulosonate in 800 ml of dimethylformamide (distilled over phosphorus pentoxide) is treated while stirring with 40 g of potassium fluoride in a four-necked flask provided with a stirrer, thermometer and calcium chloride tube. The mixture is heated to 150° C for 4 hours, cooled to room temperature and filtered. The filtrate is evaporated under reduced pressure at 50° – 60° C, the residue suspended in 250 ml of ethyl acetate and filtered. The filtrate is evaporated under reduced pressure at 50° C. There is obtained crude methyl 6-fluoro-2,3-ispropylidene-L-gulosonate as a yellow oil. This is dissolved in 150 ml of low-boiling petroleum ether/acetone (7:3 parts by volume) and purified by column chromatography on silica gel with low-boiling petroleum ether/acetone (7:3 parts by volume). The product melts at 98° – 100° C after recrystallisation from isopropyl ether/low-boiling petroleum ether.

EXAMPLE 9

In the same manner as described in Example 6, methyl 2,3-isopropylidene-6-iodo-L-gulosonate is converted to 6-deoxy-6-iodo-L-ascorbic acid of melting point 205° C (decomposition).

EXAMPLE 10

A solution of 20 g of methyl 2,3-isopropylidene-6-tosyl-L-gulosonate in 400 ml of methyl propyl ketone is treated with 37.2 g of sodium iodide in a four-necked flask provided with a stirrer, thermometer and reflux condenser. The mixture is heated under reflux for 3.5 hours, cooled to room temperature and filtered. The filter residue is washed with 50 ml of methyl propyl ketone and the filtrate evaporated under reduced pressure at 45° C. The residue is suspended in 200 ml of benzene and subsequently filtered. The filter residue is washed with 50 ml of benzene and the filtrate evaporated to dryness. The residue is dissolved in 50 ml of ethyl acetate and purified by column chromatography on silica gel with ethyl acetate. The methyl 2,3-isopropylidene-6-iodo-L-gulosonate obtained melts at 113° – 115° C after recrystallisation from diethyl ether/low-boiling petroleum ether (over carbon).

EXAMPLE 11

In the same manner as described in Example 6, methyl 6-bromo-2,3-isopropylidene-L-gulosonate is converted to 6-bromo-6-deoxy-L-ascorbic acid of melting point 175° – 176° C; $[\alpha]_D^{25} = -7.3°$ (water; c = 1).

EXAMPLE 12

A solution of 25 g of methyl 2,3-isopropylidene-L-gulosonate in 400 ml of triethylphosphate is treated while stirring with 79 g of triphenylphosphine in a four-necked flask provided with a thermometer, reflux condenser, calcium chloride tube and stirrer. 16 ml of bromine are subsequently introduced dropwise. The mixture is subsequently stirred at 80° C for 15 minutes. The mixture is cooled to room temperature, poured into 4 liters of diethyl ether while stirring, treated with 10 g of active carbon and filtered. The filtrate is evaporated under strongly reduced pressure at 80° C. The residue is treated with 200 ml of diethyl ether, filtered and again evaporated. The thus-obtained residue is dissolved in 200 ml of ethyl acetate and purified by column chromatography on silica gel with ethyl acetate. The methyl 6-bromo-2,3-isopropylidene-L-gulosonate obtained melts at 107° – 108° C after recrystallisation from an isopropyl ether/low-boiling petroleum ether mixture.

The following Example illustrates the stabilization of oxidation-sensitive organic materials using one of the halogen derivatives provided by this invention:

EXAMPLE 13

The following amounts of 6-chloro-6-deoxy-L-ascorbic acid are blended with the following oxidation-sensitive organic materials in order to stabilize said materials:

| Material | mg of 6-chloro-6-deoxy-L-ascorbic acid per kg |
| --- | --- |
| Corn oil | 100 |
| Margarine | 100 |
| Salad dressing | 200 |
| Mayonnaise | 200 |
| Chocolate | 300 |
| Skin cream | 300 |
| Lipstick | 300 |

We claim:
1. A compound of the tautomeric formulae

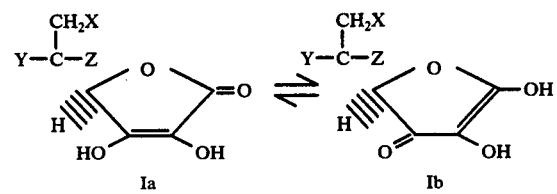

wherein X is halogen; and one of Y and Z is hydrogen, and the other is hydroxy; with the proviso that when Y is hydroxy and Z is hydrogen, X is chlorine or bromine; a salt of these compounds.

2. The compound of claim 1 wherein said compound is 6-chloro-6-deoxy-L-ascorbic acid or a salt thereof.

3. The compound of claim 1 wherein said compound is 6-bromo-6-deoxy-L-ascorbic acid or a salt thereof.

4. The compound of claim 1 wherein said compound is 6-deoxy-6-fluoro-L-ascorbic acid or a salt thereof.

5. The compound of claim 1 wherein said compound is 6-deoxy-6-iodo-L-ascorbic acid or a salt thereof.

6. Process for stabilizing oxidation-sensitive organic materials comprising incorporating in said material a stabilizing amount of a compound of the tautomeric formula:

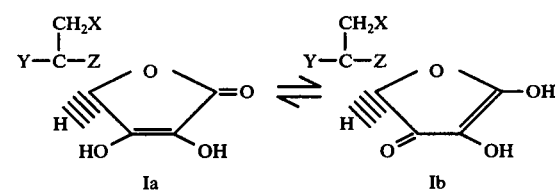

wherein X is halogen; and one of Y and Z is hydrogen and the other is hydroxy; with the proviso that when Y is hydroxy and Z is hydrogen, X is chlorine or bromine; or with a salt thereof.

7. The process of claim 6 wherein said compound is incorporated in an amount of from 0.001 wt. to 0.1 wt.% based upon the weight of said material.

8. A mixture comprising a stabilizing amount of a oxidation-sensitive organic material and a compound of the tautomeric formulae

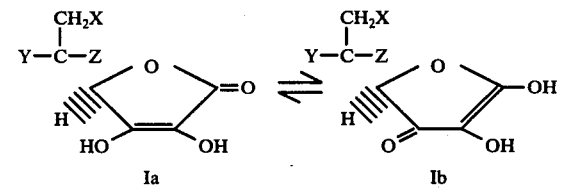

wherein X is halogen; and one of Y and Z is hydrogen atom and the other is hydroxy; with the proviso that when Y is hydroxy and Z is hydrogen, X is chlorine or bromine,
or with a salt thereof.

9. The mixture of claim 8 wherein said compound is present in an amount of from 0.001 to 0.1 wt. of the material to be stabilized.

* * * * *

UNITED STATES PATENT AND TRADEMARK OFFICE
CERTIFICATE OF CORRECTION

PATENT NO. : 4,043,937
DATED : August 23, 1977
INVENTOR(S) : Joseph Kiss et al.

It is certified that error appears in the above-identified patent and that said Letters Patent are hereby corrected as shown below:

Column 1, lines 8-16;   Column 10, claim 1, lines 1-9;   Column 10, claim 6, lines 26-34;   and Column 10, claim 8, lines 45-53:

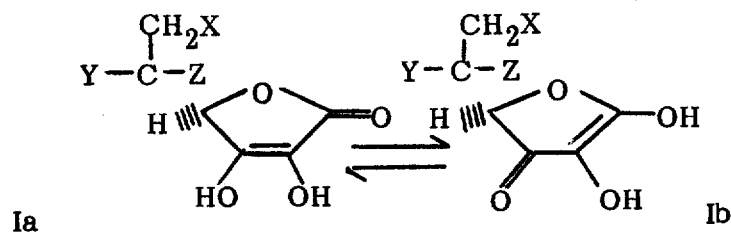

should be:

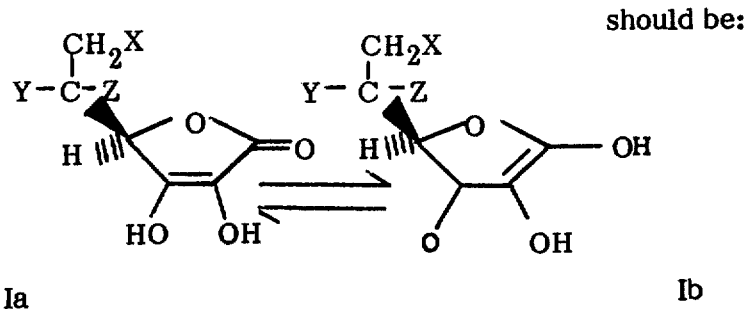

UNITED STATES PATENT AND TRADEMARK OFFICE
CERTIFICATE OF CORRECTION

PATENT NO. : 4,043,937
DATED : August 23, 1977
INVENTOR(S) : Joseph Kiss et al.

It is certified that error appears in the above-identified patent and that said Letters Patent are hereby corrected as shown below:

Column 1, lines 60-68

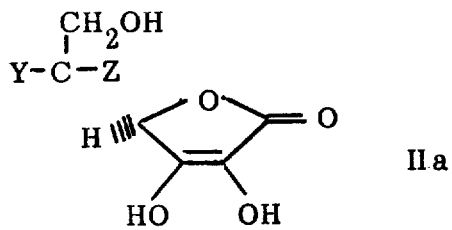

IIa should be:

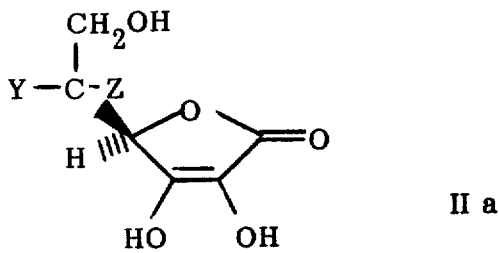

II a

UNITED STATES PATENT AND TRADEMARK OFFICE
CERTIFICATE OF CORRECTION

PATENT NO. : 4,043,937
DATED : August 23, 1977
INVENTOR(S) : Joseph Kiss et al.

It is certified that error appears in the above-identified patent and that said Letters Patent are hereby corrected as shown below:

Column 2, lines 1-9

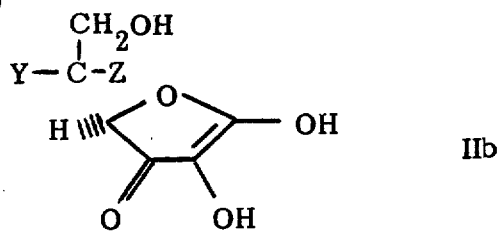

should be:

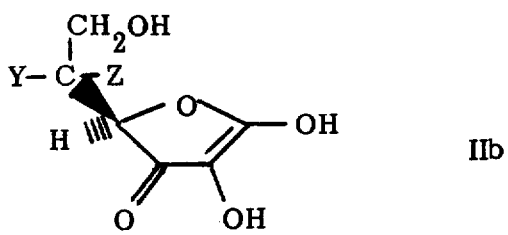

Column 10, claim 1, line 12, after "bromine;" insert — or —

Column 10, claim 7, line 40, "0.001 wt. to" should be:

0.001 wt. % to

Signed and Sealed this

Twenty-fifth Day of September 1979

[SEAL]

Attest:

LUTRELLE F. PARKER

*Attesting Officer*   *Acting Commissioner of Patents and Trademarks*